(12) United States Patent
D'Amato

(10) Patent No.: US 6,525,019 B2
(45) Date of Patent: Feb. 25, 2003

(54) USE OF MELANIN FOR INHIBITION OF ANGIOGENESIS AND MACULAR DEGENERATION

(75) Inventor: Robert J. D'Amato, Lexington, MA (US)

(73) Assignee: The Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/966,282

(22) Filed: Sep. 28, 2001

(65) Prior Publication Data

US 2002/0128304 A1 Sep. 12, 2002

Related U.S. Application Data

(63) Continuation of application No. PCT/US99/19026, filed on Aug. 20, 1999.
(60) Provisional application No. 60/097,395, filed on Aug. 21, 1998.

(51) Int. Cl.⁷ .................................. A61K 38/00
(52) U.S. Cl. ......................................... 514/2
(58) Field of Search ............................. 514/2

(56) References Cited

PUBLICATIONS

Angiolillo, A. et al. Human Interferon–inducible Protein 10 is a Potent Inhibitor of Angiogenesis in Vivo. *The Journal of Experimental Medicine* vol. 182 pp. 155–162 Jul. 1995.
Bohm, M. et al. Alpha–Melanocyte–Stimulating Hormone Modulates Activation of NF–kappa B and AP–1 and Secretion of Interleukin–8 in Human Dermal Fibroblasts *Annals of the New York Academy of Sciences* vol. 885 pp. 277–286 1999.
Cao, Y. et al. gro–B, a–C–X–C– Chemokine, is an Angiogenesis Inhibitor that Suppresses the Growth of Lewis Lung Carninoma in Mice *Journal of Experimental Medicine* vol. 182 pp. 2069–2077 Dec. 1, 1995.
Chen, C. et al. A Strategy to Discover Circulating Angiogenesis Inhibitors Generated by Human Tumors *Cancer Research* vol. 55 pp. 4230–4233 Oct. 1, 199.
Clapp, C. et al. The 16–kilodalton N–terminal Fragment Of Human Prolactin Is A Potent Inhibitor Of Angiogenesis *Endocrinology* vol. 133 pp. 1292–1299 Mar. 1, 1993.
Dameron, K.M. et al. Control of Angiogenesis in Fibroblasts by p53 Regulation of Thrombospondin–1 *Science* vol. 265 pp. 1582–1584 Sep. 9, 1994.
Folkman, J. Tumor angiogenesis and tissue factor *Nature Medicine* vol. 2 pp. 167–168 Feb. 1, 1996.
Folkman, J. What is the Evidence that Tumors are Angiogenesis Dependent? *Journal of the National Cancer Institute* vol. 82 pp. 4–6 Jan. 3, 1990.
Folkman, J. Angiogenesis and Its Inhibitors *Important Advances in Oncology* pp. 42–62 Jan. 1, 1985.

Folkman, J. et al. Long–term culture of capillary endothelial cells *Proceedings of the National Academy of Science USA* vol. 76 pp. 5217–5221 Oct. 1, 1979.
Gavrieli, Y. et al. Identification of Programmed Cell Death in Situ via Specific Labeling of Nuclear DNA Fragmentation *Journal of Cell Biology* vol. 119 pp. 493–501 1992.
Good, D.J. et al. A tumor suppressor–dependent inhibitor of angiogenesis is immunologically and functionally indistinguishable from a fragment of thombospondin *Proceedings of the National Academy of Science USA* vol. 87 pp. 6624–6628 09/90.
Goodall, T. et al. Effect of Melanocyte Stimulating Hormone on Human Cultured Choroidal Melanocytes, Uveal Melanoma Cells, and Retinal Epithelial Cells *Investigative Ophthalmology & VIsual Science* vol. 35 (1–3) pp. 826–837 Mar. 1994.
Grant, D.S. et al. Two Different Laminin Domains Mediate the Differentiation of Human Endothelial Cells into Capillary–like Structures in Vitro *Cell* vol. 58 pp. 933–943 Sep. 8, 1989.
Gross, J.L. et al. Increased capillary endothelial cell protease activity in response to angiogenic stimuli in vitro *Proceedings of the National Academy of Science USA* vol. 80 pp. 2623–2627 05/83.
Gupta, S. et al. A potent inhibitor of endothelial cell proliferation is generated by proteolytic cleavage of the chemokine platelet factor 4 *Proceedings of the National Academy of Science USA* vol. 92 pp. 7799–7803 08/95.
Hammond, B. et al. Iris Color and Macular Pigment Optical Density *Experimental Eye Research* vol. 62 (3) pp. 293–297 Mar. 1996.
Hill, H. et al. Melanin: A Two–Edged Sword? *Pigment Cell Research* vol. 10 pp. 158–161 1997.
Holmgren, L. et al. Dormancy of micrometastases: Balanced proliferation and apoptosis in the presence of angiogenesis suppression *Nature Medicine* vol. 1 (2) pp. 149–153 02/95.
Homandberg, G.A. et al. Heparin–binding Fragments of Fibronectin are Potent Inhibitors of Endothelial Cell Growth *American Journal of Pathology* vol. 120 pp. 327–332 09/85.
Hori, A. et al. Suppression of Solid Tumor Growth by Immunoneutralizing Monoclonal Antibody Against Human Basic Fibroblasts Growth Factor *Cancer Research.* vol. 51 pp. 6180–6184 Nov. 15, 1991.
Kandel, J. et al. Neovascularization is Associated with a Switch to the Export of bFGF in the Multistep Development of Fibrosarcoma *Cell* vol. 66 pp. 1095–1104 Sep. 20, 1991.
Kenyon, B. et al. A Model of Angiogenesis in the Mouse Cornea *Investigative Ophthalmology and Visual Science* vol. 37 (8) pp. 1625–1632 Jul. 1996.

(List continued on next page.)

Primary Examiner—Dwayne C. Jones
(74) Attorney, Agent, or Firm—Kilpatrick Stockton LLP

(57) ABSTRACT

Composition and methods of using melanin, or melanin-promoting compounds, for inhibiting angiogenesis to treat angiogenesis-dependent diseases, such as macular degeneration and cancer.

8 Claims, No Drawings

OTHER PUBLICATIONS

Kim, K.J. et al. Inhibition of vascular endothelial growth factor–induced angiogenesis suppresses tumor growth in Vivo *Nature* vol. 362 pp. 841–844 Apr. 29, 1993.

Maione, T.E. et al. Inhibition of Angiogenesis by Recombinant Human Platelet Factor–4 and Related Peptides *Science* vol. 247 pp. 77–79 Jan. 5, 1990.

Menon, I.A. et al. Effects of Ultraviolet–visible Irradiation in the Presence of Melanin Isolated from Human Black or Red Hair upon Ehrlich Ascites Carcinoma Cells *Cancer Research* vol. 43 (7) pp. 3165–3169 Jul. 1983.

Millauer, B. et al. Glioblastoma growth inhibited in vivo by a dominant–negative Flk–1 mutant *Nature* vol. 367 pp. 576–579 Feb. 10, 1994.

Muragaki, Y. et al. Mouse col18a1 is expressed in a tissue–specific manner as three alternative variants and is localized in basement membrane zones *Proceedings of the National Academy of Science USA* vol. 92 pp. 8763–8767 Sep. 1995.

Nelson, J. et al. Murine Epidermal Growth Factor (egf) Fragment (33–42) Inhibits Both Egf– And Laminin–dependent Endothelial Cell Motility And Angiogenesis *Cancer Research* vol. 55 pp. 3772–3776 Sep. 1, 1995.

Nguyen, M. et al. Quantitation of Angiogenesis and Anti-angiogenesis in the Chick Embryo Chorioallantoic Membrane *Microvascular Research* vol. 47 pp. 31–40 1994.

O'Reilly et al. Angiostatin induces and sustains dormancy of human primary tumors in mice *Nature Medicine* vol. 2 (6) pp. 689–692 Jun. 1996.

O'Reilly et al. Angiostatin: A Novel Angiogenesis Inhibitor that Mediates the Suppression of Metastases by a Lewis Lung Carcinoma *Cell* vol. 79 pp. 315–328 Oct. 21, 1994.

O'Reilly et al. Endostatin: An Endogenous Inhibitor of Angiogenesis and Tumor Growth *Cell* vol. 88 pp. 277–285 Jan. 24, 1997.

Obeso, J. et al. Methods in Laboratory Investigation/A Hemangioendothelioma–Derived Cell Line: Its Use as a Model for the Study of Endothelial Cell Biology *Laboratory: Investigation* vol. 63 (2) pp. 259–269 1990.

Oh, S.P. et al. Isolation and sequencing of cDNAs for proteins with multiple domains of Gly–Xaa–Yaa repeats identify a distinct family of collagenous proteins *Proceedings of the National Academy of Science USA* vol. 91 pp. 4229–4233 May 1994.

Parangi, S. et al. Antiangiogenic therapy of transgenic mice impairs de novo tumor growth *Proceedings of the National Academy of Science USA* vol. 93 pp. 2002–2007 Mar. 1996.

Pawelek, J. et al. Melanoma Cells Resistant to Inhibition of Growth by Melanocyte Stimulating Hormone *Proceedings of the National Academy of Sciences* vol. 72 (3) pp. 951–955 Mar. 1975.

Pawelek, J. et al. Molecular Controls in Mammalian Pigmentation *Yale Journal of Biology & Medicine* vol. 46 pp. 430–433 1973.

Rastinejad, F. et al. Regulation of the Activity Of A New Inhibitor Of Angiogenesis By A Cancer Suppressor Gene *Cell* vol. 56 pp. 345–355 Feb. 10, 1989.

Rehn, M. et al. α1 (XVIII), a collagen chain with frequent interruptions in the collagenous sequence, a distinct tissue distribution, and homology with type XV collagen *Proceedings of the National Academy of Science, USA* vol. 91 pp. 4234–4238 May 1994.

Rehn, M. et al. Identification of Three N–terminal Ends Of Type Xviii Collagen Chains And Tissue–specific Differences In The Expression Of The Corresponding Transcripts *Journal of Biological Chemistry* vol. 270 pp. 4705–4711 Mar. 3, 1995.

Riley, P.A. Melanogenesis: a Realistic Target for Antimelanoma Therapy? *Europenan Journal of Cancer* vol. 27 (9) pp. 1172–1177 Sep. 1991.

Sage, E.H. et al. Inhibition of Endothelial Cell Proliferation by SPARC is Mediated through a $Ca^{2+}$–Binding EF–Hand Sequence *Journal of Cellular Biochemistry* vol. 57 pp. 127–140 1995.

Sakamoto, N. et al. Inhibition of Angiogenesis And Tumor Growth By A Synthetic Laminin Peptide. Cdpgyigsr–nh2 *Cancer Research* vol. 51 pp. 903–906 Feb. 1, 1991.

Slominski et al. Inhibition of Melanogenesis for Melanoma Therapy *Journal of Investigative Dermatology* vol. 103 (5) pp. 742 Nov. 1994.

Strieter, R.M. et al. InterferonΓ–Inducible Protein 10 (IP–10), A Member of the C–X–C Chemokine Family, is an Inhibitor of Angiogenesis *Biochemistry Biophysiology Research Communications* vol. 210 pp. 51–57 May 5, 1995.

Studier, W.F. et al. Use of T7 RNA Polymerase To Direct Expression Of Cloned Genes *Methods of Enzymology* vol. 185 pp. 60–89 1990.

Teicher, B.A. et al. Potentiation of Cytotoxic Cancer Therapies by TNP–470 Alone and with other Antiangiogenic Agents *International Journal of Cancer* vol. 57 (6) pp. 920–925 1994.

Tolsma, S.S. et al. Peptides Derived From Two Separate Domains Of The Matrix Protein Thrombospondin–1 Have Antiangiogenic Activity *Journal of Cell Biology* vol. 122 pp. 497–511 Jul. 1993.

Voest, E.E. et al. Inhibition of Angiogenesis in Vivo by Interleukin 12 *Journal of the National Cancer Institute* vol. 87 pp. 581–586 Apr. 19, 1995.

Weiter et al. Relationship pf Senile Macilar Degeneration to Ocular Pigmentation *American Journal of Ophthalmology* vol. 99 pp. 185–187 Feb. 1985.

USE OF MELANIN FOR INHIBITION OF ANGIOGENESIS AND MACULAR DEGENERATION

RELATED APPLICATIONS

This application is a continuation of PCT Application No. US99/19026, filed Aug. 20, 1999, which claims the benefit of U.S. Provisional Application No. 60/097,395, filed Aug. 21, 1998.

TECHNICAL FIELD

This application relates to a inhibitor of angiogenesis useful for treating angiogenesis-related diseases, such as macular degeneration and angiogenesis-dependent cancers. The invention further relates to novel pharmaceutical compositions and methods for treating and curing macular degeneration, and other angiogenesis-dependent diseases.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In advanced age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Several lines of direct evidence now suggest that angiogenesis is essential for the growth and persistence of solid tumors and their metastases (Folkman, 1989; Hori et al., 1991; Kim et al., 1993; Millauer et al., 1994). To stimulate angiogenesis, tumors upregulate their production of a variety of angiogenic factors, including the fibroblast growth factors (FGF and BFGF) (Kandel et al., 1991) and vascular endothelial cell growth factor/vascular permeability factor (VEGF/VPF). However, many malignant tumors also generate inhibitors of angiogenesis, including angiostatin and thrombospondin (Chen et al., 1995; Good et al., 1990; O'Reilly et al., 1994). It is postulated that the angiogenic phenotype is the result of a net balance between these positive and negative regulators of neovascularization (Good et al., 1990; O'Reilly et al., 1994; Parangi et al., 1996; Rastinejad et al., 1989). Several other endogenous inhibitors of angiogenesis have been identified, although not all are associated with the presence of a tumor. These include, platelet factor 4 (Gupta et al., 1995; Maione et al., 1990), interferon-alpha, interferon-inducible protein 10 (Angiolillo et al., 1995; Strieter et al., 1995), which is induced by interleukin-12 and/or interferon-gamma (Voest et al., 1995), gro-beta (Cao et al., 1995), and the 16 kDa N-terminal fragment of prolactin (Clapp et al., 1993). The only known angiogenesis inhibitors which specifically inhibit endothelial cell proliferation are angiostatin™ protein (O'Reilly et al. 1994) and endostatin™ protein (O'Reilly et al. 1997).

Thus, new methods and compositions are needed that are capable of inhibiting angiogenesis and treating angiogenesis-dependent diseases.

Melanin belongs to a ubiquitous family of pigments found throughout the mammalian organism located within specific cells called melanocytes. The two primary types of melanins are eumelanin, which include brown and black pigments, and pheomelanin, which are red and yellow pigments. Melanins are present in the skin, hair and eyes where they are responsible for color and playing a role in light absorption and free-radical scavenging.

As a chemical group, melanins comprise a high proportion of indoles which can copolymerise with other residues to give a wide range of macromolecular pigments. Indolic melanin is metabolically derived from the amino acid L-tyrosine by a multi-step process all of which is not completely eulicidated. There is an initial oxidation reaction, which involves ring hydroxylation and dehydrogenation of tyrosine to form the intermediate, dopaquinone or L-phenylalanine-3,4-orthoquinone. This important reaction is catalyzed by the enzyme tyrosinase. Tyrosinase is also able to oxidize a wide range of analogous phenols and catechols. The resulting orthoquinones are highly reactive molecules which can readily undergo redox reactions and combination with nucleophiles. These intermediates are hypothesized to go through a number of reduction and polymerization reactions eventually leading to the formation of melanin. Though all of the intermediate steps leading to the formation of melanin are not clearly defined, it is known that melanogenesis involves the formation of several highly interactive compounds which can constitute a potential hazard to melanocytes.

Melanin pigments play a critical role in the development of skin cancers such as melanoma, which involves tumor development from transformed melanocytes. Light-skinned individuals with more pheomelanin tend to have a higher incidence of melanoma than darker skinned individuals, perhaps due to greater amounts of eumelanin present in the latter. This also may be due to the fact the pheomelanin is more sensitive to ultraviolet (UV) irradiation than eumelanin with a greater production of superoxide free-radicals formed when the lighter pigments are irradiated (Menon et al., 1983).

Malignant melanomas of the pigmented choroid of the eye are the most common primary intraocular malignancies in adults most likely resulting from a loss of metabolic regulatory control in melanocytes (Goodall 1994). Evidence from the relevant literature has suggested that individuals with increased iris pigmentation have a decreased risk of developing macular degeneration. Since increased levels of eumelanin appear to be more protective than pheomelanin, the light-absorbing characteristics of melanin are thought to be responsible for this protective effect (Hammond et al., 1996; Weiter et al., 1985). An alternative hypothesis presented by Weiter and colleagues is that increased levels of melanin may protect against age-related increases in lipofusion (implicated in photo-oxidative mechanisms). Weiter, et al., at 186. However, these prior studies do not teach, discuss, or suggest the antiangiogenic ability of melanin to inhibit blood vessel growth and macular degeneration, as disclosed in the current invention.

Melanocyte stimulating hormone (MSH) has been demonstrated to increase tyrosinase activity, increase cellular melanin content, and increase the number of melanocytes via a cAMP mediated mechanism. (Pawlek et al., 1973). MSH acts via specific cell-surface receptors on melanocytes and melanoma cells. MSH has been shown to have the dual and contradictory effect of inhibiting the growth of melanoma cells in vitro (but not in vivo) while stimulating melanin producing melanocytes. (Pawleck et al., 1975). These effects have been suggested to be related to either the presence or absence of amino acid precursors or metabolic intermediates. Anecdotal evidence has suggested that L-DOPA administration in Parkinson's' disease increases the risk factors for developing melanoma while inhibition of melanogenesis via restriction of L-phenylalanine and L-tyrosine, or inhibition of tyrosinase, can slow or even reverse the progression of melanoma in humans (Salominski and Paus, 1994). Therefore, it has been suggested that decreasing dietary amino acids will lead to inhibition of melanoma growth, yet others have suggested that increased levels of precursor amino acids (but not melanin itself) will lead to melanocytotoxcity. (Riley, 1991). Thus melanin, with roles as both a photo sensitizer and protector has been called a "two edged sword." (Hill et al., 1997).

The prior art in the field has suggested that decreasing melanin synthesis or increasing intermediate formation will lead to melanotoxicty and decrease in the size of melanomas. This teaches away the current invention in which increased levels of melanin are disclosed to decrease angiogenesis (blood vessel formation in tumors) and thus lead to decreased tumor size and formation.

SUMMARY OF THE INVENTION

The present invention relates to a novel angiogenesis inhibitor, and method for its use. In particular, therapy with the inhibitor exhibits strong anti-macular degeneration activity.

The invention provides compositions and methods of using melanin, including eumelanin and phaeomelanin, and soluble and insoluble forms of melanin, precursors or fragments thereof, and melanin-promoting compounds to inhibit angiogenesis, and in particular to treat macular degeneration. By melanin-promoting compounds is meant any compounds which stimulate the expression of melanin in an individual, such as tyrosinase, MSH (melanocyte stimulating hormone), or MCH (melanocyte concentrating hormone). Therefore, a preferred angiogenesis inhibitor is melanin, however, the invention also contemplates that other compounds causing an increase in melanin may be used to inhibit angiogenesis, and particularly to treat macular degeneration.

The present invention provides methods and compositions for treating diseases and processes mediated by undesired and uncontrolled angiogenesis by administering to a human or animal with the undesired angiogenesis a composition comprising melanin, or melanin-promoting compound, in a dosage sufficient to inhibit angiogenesis. The present invention is particularly useful for treating or for repressing macular degeneration. Administration of melanin, or a melanin-promoting compound to a human or animal with prevascularized metastasized tumors prevents the growth or expansion of those tumors.

The present invention also includes diagnostic methods and kits for detection and measurement of melanin, or a melanin-promoting compound, in biological fluids and tissues, and for localization of melanin, or a melanin-promoting compound, in tissues. The diagnostic method and kit can be in any configuration well known to those of ordinary skill in the art. The present invention also includes antibodies specific for the melanin, or a melanin-promoting compound, and antibodies that inhibit the binding of antibodies specific for the melanin, or a melanin-promoting compound. These antibodies can be polyclonal antibodies or monoclonal antibodies. The antibodies specific for melanin, or a melanin-promoting compound, can be used in diagnostic kits to detect the presence and quantity of melanin, or a melanin-promoting compound, which is diagnostic or prognostic for the occurrence or recurrence of cancer or other disease mediated by angiogenesis. Antibodies specific for melanin, or a melanin-promoting compound, may also be administered to a human or animal to passively immunize the human or animal against melanin, or a melanin-promoting compound, thereby reducing angiogenic inhibition.

The present invention also includes melanin, or a melanin-promoting compound, that can be labeled isotopically or with other molecules or proteins for use in the detection and visualization of melanin, or a melanin-promoting compound, sites with state of the art techniques, including, but not limited to, positron emission tomography, autoradiography, flow cytometry, radioreceptor binding assays, and immunohistochemistry.

These melanin and melanin-promoting compounds also act as agonists and antagonists at the melanin receptor, thereby enhancing or blocking the biological activity of melanin, or a melanin-promoting compound.

The present invention also relates to methods of using the melanin, or a melanin-promoting compound, fragments, and antibodies that bind specifically to the inhibitor and its fragments, to diagnose endothelial cell-related diseases and disorders.

Accordingly, it is an object of the present invention to provide a pharmaceutical composition comprising a melanin, or a melanin-promoting compound.

It is another object of the present invention to provide a method of treating diseases and processes that are mediated by angiogenesis.

It is yet another object of the present invention to provide a diagnostic or prognostic method and kit for detecting the presence and amount of melanin, or a melanin-promoting compound, in a body fluid or tissue.

It is yet another object of the present invention to provide a method and composition for treating diseases and processes that are mediated by angiogenesis including, but not limited to macular degeneration, corneal diseases, rubeosis, neovascular glaucoma, diabetic retinopathy, retrolental fibroplasia, hemangioma, solid tumors, leukemia, metastasis, telangiectasia psoriasis scleroderma, pyogenic granuloma, myocardial angiogenesis, plaque neovascularization, coromay collaterals, cerebral collaterals, arteriovenous malformations, ischemic limb angiogenesis, arthritis, diabetic neovascularization, wound healing, peptic ulcer, fractures, keloids, vasculogenesis, hematopoiesis, ovulation, menstruation, and placentation.

It is another object of the present invention to provide a composition for treating or repressing the growth of a cancer.

It is an object of present invention to provide a method for detecting and quantifying the presence of an antibody specific for an melanin, or a melanin-promoting compound, in a body fluid.

Still another object of the present invention is to provide a composition consisting of antibodies to melanin, or a melanin-promoting compound, that are selective for specific regions of the melanin, or a melanin-promoting compound, molecule.

It is another object of the present invention to provide a method for the detection or prognosis of cancer.

It is another object of the present invention to provide a composition for use in visualizing and quantitating sites of melanin, or a melanin-promoting compound, binding in vivo and in vitro.

It is yet another object of the present invention to provide a composition for use in detection and quantification of melanin, or a melanin-promoting compound, biosynthesis.

It is yet another object of the present invention to provide a therapy for macular degeneration that has minimal side effects.

Still another object of the present invention is to provide a composition comprising melanin, or a melanin-promoting compound, linked to a cytotoxic agent for treating or repressing the growth of a cancer.

These and other objects, features and advantages of the present invention will become apparent after a review of the following detailed description of the disclosed embodiments and the appended claims.

DETAILED DESCRIPTION OF THE INVENTION

Applicants have discovered that a class of compounds has the ability to inhibit endothelial proliferation when added to proliferating endothelial cells in vitro. These compounds capable of inhibiting angiogenesis are melanin and melanin-promoting compounds. The inhibitor compounds of the invention are useful for treating angiogenesis-related diseases, particularly macular degeneration, and angiogenesis-dependent cancers and tumors. The unexpected and surprising ability of melanin to treat and cure angiogenesis-dependent diseases answers a long felt and unfulfilled need in the medical arts, and provides an important benefit to mankind.

It will be appreciated that the term "melanin" as used herein means both soluble and insoluble forms of melanin, including eumelanin and phaeomelanin, and precursors or fragments of these molecules. The term "melanin-promoting compound" as used herein means any compound capable of increasing the amount or activity of melanin in vivo. Examples of melanin-promoting compounds are tyrosinase, melanocyte stimulating hormone (MSH), melanocyte concentrating hormone (MCH), minocycline, latanoprost, melanotan-I, prostaglandins and compounds with prostaglandin activity, ACTH, melanocortin receptor antagonists, endothelin, rifabutin, diacycloglycerols, arbutin, amiodarone, pefloxcin, chlorpromazine, desipramine, sulfasalazine, zidovudine, clofazimine, bergapten, metenkephalin and cyclophosphamide. Such alternative compounds may modify the production or bioactivity of melanin.

Melanin-promoting compounds may be quickly and easily tested for endothelial proliferation inhibiting activity using a biological activity assay such as the bovine capillary endothelial cell proliferation assay. Other bioassays for inhibiting activity include the chick CAM assay, the mouse corneal assay, and the effect of administering isolated or synthesized proteins on implanted tumors. The chick CAM assay is described by O'Reilly, et al. in "Angiogenic Regulation of Metastatic Growth" *Cell* vol. 79 (2), Oct. 21, 1994, pp. 315–328, which is hereby incorporated by reference in its entirety. Briefly, 3 day old chicken embryos with intact yolks are separated from the egg and placed in a petri dish. After 3 days of incubation a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Important terms that are used herein are defined as follows. "Cancer" means angiogenesis-dependent cancers and tumors, i.e. tumors that require for their growth (expansion in volume and/or mass) an increase in the number and density of the blood vessels supplying then with blood. "Regression" refers to the reduction of tumor mass and size.

The present invention also includes the detection of melanin, or a melanin-promoting compound, in body fluids and tissues for the purpose of diagnosis or prognosis of angiogenesis-mediated diseases such as cancer. The present invention also includes the detection of melanin, or a melanin-promoting compound, binding sites and receptors in cells and tissues. The present invention also includes methods of treating or preventing angiogenic diseases and processes including, but not limited to, macular degeneration and tumors by stimulating the production of melanin, and/or by administering substantially purified melanin, or a melanin-associated compound, or a fusion protein containing the same, to a patient. Additional treatment methods include administration of melanin, or a melanin-associated compound, or a fusion protein containing the same, linked to cytotoxic agents.

Passive antibody therapy using antibodies that specifically bind melanin can be employed to modulate endothelial-dependent processes such as reproduction, development, and wound healing and tissue repair. Antibodies specific for melanin, or a melanin-promoting compound, are made according to techniques and protocols well-known in the art. The antibodies may be either polyclonal or monoclonal. The antibodies are utilized in well-know immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva, and mucus.

Angiogenesis-related diseases may be diagnosed and treated using the endothelial cell proliferation inhibiting compounds of the present invention. Angiogenesis-related diseases include, but are not limited to, ocular angiogenic diseases, for example, diabetic retinopathy, retinopathy of prematurity, macular degeneration, corneal graft rejection, neovascular glaucoma, retrolental fibroplasia, rubeosis; angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; Osler-Webber Syndrome; myocardial angiogenesis; plaque neovascularization; telangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helobacter pylori*).

The endothelial cell proliferation inhibiting compounds can be used as a birth control agent by reducing or preventing uterine vascularization required for embryo implantation. Thus, the present invention provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possible a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that administration will interfere with normal enhanced vascularization of the placenta, and also with the development of vessels within a successfully implanted blastocyst and developing embryo and fetus.

Conversely, blockade of melanin, or a melanin-promoting compound, or receptors with melanin, which act as receptor antagonists may promote endothelialization and vascularization. Such effects may be desirable in situations of inadequate vascularization of the uterine endometrium and associated infertilty, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

It is contemplated as part of the present invention that a melanin-promoting compound, such as tyrosinase, can be produced by recombinant DNA methods, including in vivo gene expression therapy, or synthetic peptide chemical methods that are well-known to those of ordinary skill in the art. Purification methods are well-known in the art and a specific example of a method for purifying melanin, or a melanin-promoting compound, and assaying for inhibitor activity is provided in the examples below. Isolation of human endogenous melanin, or a melanin-promoting compound, is accomplished using similar techniques.

Cytotoxic agents, such as ricin, are linked to melanin, thereby providing a tool for destruction of cells that bind melanin. These cells may be found in many locations, including but not limited to, micrometastases and primary tumors. Peptides linked to cytotoxic agents are infused in a manner designed to maximize delivery to the desired location. For example, ricin-linked high affinity melanin fragments are delivered through a cannula into vessels supplying the target site or directly into the target. Such agents are also delivered in a controlled manner through osmotic pumps coupled to infusion cannulae. A combination of melanin antagonists may be co-applied with stimulators of angiogenesis to increase vascularization of tissue. This therapeutic regimen provides an effective means of destroying metastatic cancer.

According to the present invention, melanin, or a melanin-promoting compound, may be used in combination with other compositions and procedures for the treatment of diseases. For example, a tumor may be treated conventionally with surgery, radiation or chemotherapy combined with melanin, and then another anti-angiogenic compound may be subsequently administered to the patient to extend the dormancy of micrometastases and to stabilize any residual primary tumor.

Melanin, or a melanin-promoting compound, described above can be provided as substantially purified and placed in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the melanin, or a melanin-promoting compound, may be incorporated into biodegradable polymers allowing for sustained release of the compound, the polymers being implanted in the vicinity of where drug delivery is desired, for example, at the site of a tumor or implanted so that the endostatin is slowly released systemically. Osmotic minipumps may also be used to provide controlled delivery of high concentrations of melanin, or a melanin-promoting compound, through cannulae to the site of interest, such as directly into a metastatic growth or into the vascular supply to that tumor.

The dosage of the melanin, or melanin-promoting compound, of the present invention will depend on the disease state or condition being treated and other clinical factors such as weight and condition of the human or animal and the route of administration of the compound. Depending upon the half-life of the compound in the particular animal or human, it can be administered between several times per day to once a week. It is to be understood that the present invention has application for both human and veterinary use. The methods of the present invention contemplate single as well as multiple administrations, given either simultaneously or over an extended period of time.

The melanin, or melanin-promoting compound, formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The melanin, or a melanin-promoting compound, formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. In particular, intraocular injections of melanin, or melanin promoting compounds, are contemplated for the treatment of macular degeneration.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Melanin, or melanin-promoting compounds, can be coupled to other molecules using standard methods. The coupling technique is chosen on the basis of the functional groups available on the molecule. Various reagents used to effect these couplings include among others, glutaraldehyde, diazotized benzidine, carbodiimide, and p-benzoquinone.

Kits for measurement of melanin, or a melanin-promoting compound, are also contemplated as part of the present invention. Antisera that possess the highest titer and specificity and can detect the compound in extracts of plasma, urine, tissues, and in cell culture media are further examined to establish easy to use kits for rapid, reliable, sensitive, and specific measurement and localization. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity. One example of an assay kit commonly used in research and in the clinic is a radioimmunoassay (RIA) kit.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Angiogenesis Inhibitory Effect of Melanin

To determine the antagonistic effect of melanin on angiogenesis, several stains of mice were selected, having genetically similar identities, except for the ability to produce melanin. These experiments utilized pigmented C57b16 mice and substrain c57b16J/Tyr-c mice having a mutation in tyrosinase, the enzyme responsible for producing melanin, which makes them albinos. Additionally, these experiments utilized 129J mice, which are normally albinos, and compared them to 129/SV+p+Tyr-c, which have restored melanin synthesis and are pigmented.

Pellets of bovine fibroblast growth factor (bFGF) were placed in the corneas of all animals according to the well-known corneal micropocket assay described in Kenyon et al., *Invest. Ophthal.* 37(8): 1625–1632 (1996), incorporated herein by reference. The purpose of the bFGF pellet is to induce blood vessel growth in the iris, which lies just below the corneal pellet.

In pigmented mice (C57b6 and 129/SV+p+Tyr-c), vessel growth in the iris was rarely observed by biomicroscopy. In genetically similar mice that were albinos, blood vessel growth on the iris accompanied by bleeding was seen in almost all the animals.

TABLE I

| | Iris Vessel Growth and Bleeding | Percentage |
| --- | --- | --- |
| Pigmented mice | | |
| C57b16 | 0/8 | 0 |
| 129/SV + p + Tyr-c | 2/17 | 12% |
| Genetically Similar Albinos | | |
| c57b16/Tyr-c | 7/8 | 88% |
| 129J | 17/18 | 94% |

Thus, in similar genetic backgrounds, the presence of melanin in the iris will block the growth of blood vessels, or angiogenesis, in the iris and subsequent bleeding. The length of blood vessel growth was measured in the corneas of the animals and found to be statistically similar for all 4 substrains in these experiments. This could be predicted, since the cornea does not have pigmentation, and would not be expected to be affected by genetically changing the degree of pigmentation in the animals. The overall results of the experiment demonstrate that the presence of melanin in the iris specifically inhibited vessel growth selectively in this tissue.

In further experiments in albino mice, it has been demonstrated that the addition of melanin (38 mg synthetic) to the cornea decreases the ability of bFGF pellets to induce angiogenesis. Corneal angiogenesis was inhibited 24% when melanin was introduced into the cornea, relative to non-melanin controls.

The clinical correlate to these experimental findings is the observation that black patients with age related macular degeneration have a very low incidence of blood vessel growth in the pigmented layer of the eye, or choroid, compared to white patients. Additionally, black patients have a reduced incidence of vascular tumors in the skin such as childhood hemangiomas. However, there are other inherent racial differences between white and black individuals besides pigmentation, and this observation alone would be insufficient to draw the conclusions provided and demonstrated by the present invention.

The present data indicates that increasing melanin in tissues, with all other factors constant, will serve to suppress angiogenic dependent diseases therein.

REFERENCES

The following references are hereby incorporated by reference herein in their entirety.

Angiolillo, A. L., Sgadari, C., Taub, D. D., Liao, F., Farber, J. M., Miaheshwari, S., Kleinman, H. K., Reaman, G. H., and Tosato, G. (1995). Human interferon-inducible protein 10 is a potent inhibitor of angiogenesis in vivo. J. Exp. Med. 182, 155–162.

Cao, Y., Chen, C., Weatherbee, J. A., Tsang, M., and Folkman, J. (1995). Gro-beta, a C-X-C chemokine, is an angiogenesis inhibitor that suppresses the growth of Lewis lung carcinoma in mice. J. Exp. Med. 182, 2069–2077.

Chen, C., Parangi, S., Tolentino, M. J., and Folkman, J. (1995). A strategy to discover circulating angiogenesis inhibitors generated by human tumors. Cancer Res. 55, 4230–4233.

Clapp, C., Martial, J. A., Guzman, R. C., Rentier-Delrue, F., and Weiner, R. 1. (1993). The 16-kilodalton N-terminal fragment of human prolactin is a potent inhibitor of angiogenesis. Endocrinology 133, 1292–1299.

Dameron, K. M., Volpert, O. V., Tainsky, M. A., and Bouck, N. (1994). Control of angiogenesis in fibroblasts by p53 regulation of thrombospondin-1. Science 265, 1582.

Folkman, J. (1996). Tumor angiogenesis and tissue factor. Nature Med. 2, 167–168.

Folkman, J. (1989). What is the evidence that tumors are angiogenesis dependent?. J. Natl. Cancer Inst. 82, 4–6.

Folkman, J. (1985). Angiogenesis and its inhibitors. In Important Advances in Oncology 1985, V. T. DeVita, S. Hellman, and S. Rosenberg, eds. (Philadelphia: J. B. Lippincott Company), pp. 42–62.

Folkman, J., Haundenschild, C. C., and Zetter, B. R. (1979). Long-term culture of capillary endothelial cells. Proc. Natl. Acad. Sci. USA 76, 5217–5221.

Gavrieli, Y., Sherman, Y., and Ben-Sasson, S. A. (1992). Identification of programmed cell death in situ via specific labeling of nuclear DNA fragmentation. J. Cell Biol.. 119, 493–501.

Good, D. J., Polverini, P. J., Rastinejad, F., Le Beau, M. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc. Nat. Acad. Sci. USA. 87, 6624–6628.

Goodall, et al. (1994), 35 Invest Ophthalmol. Vis. Sci. 826.

Grant, D. S., Tashiro, K.-l., Sequi-Real, B., Yamada, Y., Martin, G. R., and Kleinman, H. K. (1989). Two different laminin domains mediate the differentiation of human endothelial cells into capillary-like structures in vitro. Cell 58, 933–943.

Gross, J. L., Moscatelli, D., and Rifkin, D. B. (1983). Increased capillary endothelial cell protease activity in response to angiogenic stimuli in vitro. Proc. Natl. Acad. Sci. USA 80, 2623–2627.

Gupta, S. K., Hassel, T., and Singh, J. P. (1995). A potent inhibitor of endothelial cell proliferation is generated by proteolytic cleavage of the chemokine platelet factor 4. Proc. Natl. Acad. Sci. USA 92, 7799–7803.

Hammond, et al., (1996) 62 Exp. Eye Res. 293.

Hill et al., (1997) 10 Pigment Cell Res. 158.

Holmgren, L., O'Reilly, M. S., and Folkman, J. (1995). Dormancy of micrometastases: balanced proliferation and apoptosis in the presence of angiogenesis suppression. Nature Med. 1, 149–153.

Homandberg, G. A., Williams, J. E., Grant, D., B., S., and Eisenstein, R. (1985). Heparin-binding fragments of fibronectin are potent inhibitors of endothelial cell growth. Am. J. Path. 120, 327–332.

Hori, A., Sasada, R., Matsutani, E., Naito, K., Sakura, Y., Fujita, T., and Kozai, Y. (1991). Suppression of solid tumor growth by immunoneutralizing monoclonal antibody against human basic fibroblast growth factor. Cancer Res. 51, 6180–6184.

Kandel, J., Bossy-Wetzel, E., Radvany, F., Klagsburn, M., Folkman, J., and Hanahan, D. (1991). Neovascularization is associated with a switch to the export of bFGF in the multistep development of fibrosarcoma. Cell 66, 1095–1104.

Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841–844.

Maione, T. E., Gray, G. S., Petro, J., Hunt, A. J., Donner, A. L., Bauer, S. I., Carson, H. F., and Sharpe, R. J. (1990). Inhibition of angiogenesis by recombinant human platelet factor-4 and related peptides. Science 247, 77–79.

Menon, et al. (1983), 443 Cancer Research 3165.

Millauer, B., Shawver, L. K., Plate, K. H., Risau, W., and Ullrich, A. (1994). Glioblastoma growth inhibited in vivo by a dominant-negative Flk-1 mutant. Nature 367, 576–579.

Muragaki, Y., Timmons, S., Griffith, C. M., Oh, S. P., Fadel, B., Quertemmous, T., and Olsen, B. -R. (1995). Mouse col18a1 is expressed in a tissue-specific manner as three alternative variants and is localized in basement membrane zones. Proc. Natl. Acad. Sci. USA 92, 8763–8767.

Nelson, J., Allen, W. E., Scott, W. N., Bailie, J. R., Walker, B., and McFerran, N. V. (1995). Murine epidermal growth factor (EGF) fragment (33–42) inhibits both EGF- and laminin-dependent endothelial cell motility and angiogenesis. Cancer Res. 55, 3772–3776.

Nguyen, M., Shing, Y., and Folkman, J. (1994). Quantitation of angiogenesis and antiangiogenesis in the chick embryo chorioallantoic membrane. Microvascular Res. 47, 31–40.

O'Reilly, M. S., Boehm, T., Shing, Y., Fukai, N., Vasios, G., Lane, W. S., Flynn, E., Birkhead, J. R., Olsen, B. J., Folkman, J. (1997). Endostatin: An endogenous inhibitor of angiogenesis and tumor growth. Cell 88, 277–285.

O'Reilly, M. S., Holmgren, L., Chen, C. C., and Folkman, J. (1996). Angiostatin induces and sustains dormancy of human primary tumors in mice. Nature Med. 2, 689–692.

O'Reilly, M. S., Holmgren, L., Shing, Y., Chen, C., Rosenthal, R. A., Moses, M., Lane, W. S., Cao, Y., Sage, E. H., and Folkman, J. (1994). Angiostatin: A novel angiogenesis inhibitor that mediates the suppression of metastases by a Lewis lung carcinoma. Cell 79, 315–328.

Obeso, J., Weber, J., and Auerbach. R. (1990). A hemangioendothelioma-derived cell line: its use as a model for the study of endothelial cell biology. Lab. Invest. 63, 259–269.

Oh, S. K., Kamagata, Y., Muragaki, Y., Timmons, S., Ooshima, A., and Olsen, B. R. (1994). Isolation and sequencing of cDNAs for proteins with multiple domains of GlyXaa-Yaa repeats identify a distinct family of collagenous proteins. Proc. Natl. Acad. Sci. USA 91, 4229–4233.

Parangi, S., O'Reilly, M., Christofori, G., Holmgren, L., Grosfeld, J., Folkman, J., and Hanahan, D. (1996). Anti-angiogenic therapy of transgenic mice impairs de novo tumor growth. Proc. Natl. Acad. Sci. USA 93, 2002–2007.

Pawlek et al., (1973) 46 Yale J. Bio-Med. 430.

Pawleck et al., (1975) 72 Proc. Nat. Acad. Sci. USA 951.

Rastinejad, F., Polverini, P. J., and Bouck, N. P. (1989). Regulation of the activity of a new inhibitor of angiogenesis by a cancer suppressor gene. Cell 56, 345–355.

Rehn, M., and Pihlajaniemi, T. (1994). al(XVIII), a collagen chain with frequent interruptions in the collagenous sequence, a distinct tissue distribution, and homology with type XV collagen. Proc. Natl. Acad. Sci. USA 91, 4234–4238.

Rehn, M., and Pihlajaniemi, T. (1995). Identification of three N-terminal ends of type XVIII collagen chains and tissue-specific differences in the expression of the corresponding transcripts. J. Biol. Chem. 270, 4705–4711.

Riley, (1991) 27 Eur. J. Cancer 1172.

Sage, E. H., Bassuk, J. A., Vost, J. C., Folkman. M. J., and Lane, T. F. (1995). Inhibition of endothelial cell proliferation by SPARC is mediated through a Ca (2+)-binding EF-hand sequence. J. Cell Biochem. 57, 127–140.

Sakamato, N., Iwahana, M., Tanaka, N. G., and Osaka, 8. (1991). Inhibition of angiogenesis and tumor growth by a synthetic laminin peptide, CDPGYIGSR-NH$_2$. Cancer Res. 51, 903–906.

Salominski and Paus, (1994) 103 J. Invest. Derm. 742.

Strieter, R. M., Kunkel, S. L., Arenberg, D. A., Burdick, M. D., and Polverini, P. J. (1995). Human interferon-inducible protein 10 (IP-10), a member of the C-X-C chemokine family, is an inhibitor of angiogenesis. Biochem. Biophys. Res. Comm. 210, 51–57.

Studier, W. F., Rosenberg, A. H., Dunn, J. J., and Dudendorf, J. W. (1990). Use of T7 RNA polymerase to direct expression of cloned genes. Methods Enzymol. 85, 60–89.

Teicher, B. A., Holden, S. A., Ara, G., Sotomayor, E. A., and Dong, H. Z. (1994). Potentiation of cytotoxic cancer therapies by TNP-470 alone and with other antiangiogenic agents. Int. J. Cancer 57, 1–6.

Tolsma, S. S., Volpert, O. V., Good, D. J., Frazier, W. A., Polverini, P. J., and Bouck, N. (1993). Peptides derived from two separate domains of the matrix protein thrombospondin-1 have antiangiogenic activity. J. Cell Biol. 122, 497–511.

Voest, E. E., Kenyon, B. M., O'Reilly, M. S., Truitt, G., D'Amato, R. J., and Folkman, J. (1995). Inhibition of angiogenesis in vivo by interleukin 12. J. Natl. Cancer Inst. 87, 581–586.

Weiter, et al., (1985) 99 Am. J. Ophthal 185.

What is claimed is:

1. A method of inhibiting angiogenesis in an individual comprising administering to an individual an angiogenesis inhibiting amount of melanin.

2. A method of inhibiting angiogenesis in an individual comprising administering to an individual an angiogenesis inhibiting amount of a melanin-promoting compound.

3. A method of treating macular degeneration in an individual comprising administering to an individual a macular degeneration inhibiting amount of melanin.

4. A method of treating macular degeneration in an individual comprising administering to an individual a macular degeneration inhibiting amount of a melanin-promoting compound.

5. The method of claim 1, wherein the angiogenesis causes an angiogenesis dependent disease.

6. The method of claim 2, wherein the angiogenesis causes an angiogenesis dependent disease.

7. The method of claim 5, wherein the angiogenesis dependent disease is ocular angiogenic diseases, diabetic retinopathy, retinopathy of prematurity, corneal graft rejection, neovascular glaucoma, retrolental fibroplasias, rubeosis, solid tumors, blood born tumors, leukemias, tumor metastases, benign tumors, acoustic neuromas, neurofibromas, trachomas, pyogenic granulomas, rheumatoid arthritis, psoriasis, Osler-Webber Syndrome, myocardial angiogenesis, plaque neovascularization, telangiectasia, hemophiliac joints, angiofibroma, or wound granulation.

8. The method of claim 6, wherein the angiogenesis dependent disease is ocular angiogenic diseases, diabetic retinopathy, retinopathy of prematurity, corneal graft rejection, neovascular glaucoma, retrolental fibroplasias, rubeosis, solid tumors, blood born tumors, leukemias, tumor metastases, benign tumors, acoustic neuromas, neurofibromas, trachomas, pyogenic granulomas, rheumatoid arthritis, psoriasis, Osler-Webber Syndrome, myocardial angiogenesis, plaque neovascularization, telangiectasia, hemophiliac joints, angiofibroma, or wound granulation.

* * * * *